(12) United States Patent
Baumgartner

(10) Patent No.: US 6,942,961 B1
(45) Date of Patent: Sep. 13, 2005

(54) METHOD FOR DEHYDRATING BIOLOGICAL TISSUE FOR PRODUCING PRESERVED TRANSPLANTS

(75) Inventor: Ludwig Baumgartner, Nuremberg (DE)

(73) Assignee: Tutogen Medical GmbH, Neunkirchen am Brand (DE)

( * ) Notice: Subject to any disclaimer, the term of this patent is extended or adjusted under 35 U.S.C. 154(b) by 276 days.

(21) Appl. No.: 10/049,923

(22) PCT Filed: Jul. 24, 2000

(86) PCT No.: PCT/EP00/07078

§ 371 (c)(1),
(2), (4) Date: Apr. 24, 2002

(87) PCT Pub. No.: WO01/13718

PCT Pub. Date: Mar. 1, 2001

(30) Foreign Application Priority Data

Aug. 26, 1999 (DE) .............................. 199 40 426

(51) Int. Cl.[7] ........................... A01N 1/00; A01N 1/02; C14C 1/00; C12N 5/00; C12N 5/02
(52) U.S. Cl. .................... 435/1.1; 8/94.15; 8/94.18; 435/1.3; 435/325
(58) Field of Search .............................. 435/274, 325, 435/1.1, 1.3; 8/94.15, 94.18

(56) References Cited

U.S. PATENT DOCUMENTS

| | | | |
|---|---|---|---|
| 2,681,298 A | * | 6/1954 | Ferrari |
| 3,127,317 A | * | 3/1964 | Kern et al. |
| 5,116,552 A | | 5/1992 | Morita et al. ................ 264/28 |
| 5,782,914 A | * | 7/1998 | Schankereli |
| 5,800,978 A | | 9/1998 | Goodrich, Jr. et al. .......... 435/2 |
| 6,187,137 B1 | * | 2/2001 | Druecke et al. |

FOREIGN PATENT DOCUMENTS

| | | |
|---|---|---|
| DE | 29 06 650 C2 | 5/1989 |
| DE | 2906650 C2 | 5/1989 |
| DE | 38 35 237 C1 | 12/1989 |
| DE | 3835237 C1 | 12/1989 |
| DE | 44 04 625 C2 | 10/1996 |
| DE | 4404625 C2 | 10/1996 |

OTHER PUBLICATIONS

Lee, "Optimal Conditions for Long Term Storage of Native Collagens", Collagen Rel. Res. vol. 3 1983, pp. 305-315.
Pelker et al., "Biomechanical Prperties of Bone Allografts", Clinical Orthopedics and Related Research, No. 174, Apr. 1983, pp. 54-57.
Terracio et al., "Ultrastructural Observations on Tissues Processed by a Quick-Freezing, Rapid-Drying Method: Comparisons with Conventional Specimen Preparation", Cryobiology 18, 55-71 (1981).
Peters et al., "Freeze-Substitution of Chemically Stabilized Samples for Biological Field Emission Scanning Electron Microscopy", Microscopy Research and Technique 22:170-184 (1992).
Tan, "Preservation of Fungi", Cryptogamie, Mycol. 1997, 18(2):157-163.

* cited by examiner

*Primary Examiner*—David M. Naff
*Assistant Examiner*—Deborah K. Ware
(74) *Attorney, Agent, or Firm*—Gifford, Krass, Groh, Sprinkle, Anderson & Citkowski, P.C.

(57) ABSTRACT

The invention relates to a two-step method for dehydrating biological tissues for producing preserved transplants. In a first step, the tissue is partially dehydrated with an organic, water-miscible solvent. In a second step, the tissue is dehydrated further by freeze drying.

7 Claims, 2 Drawing Sheets

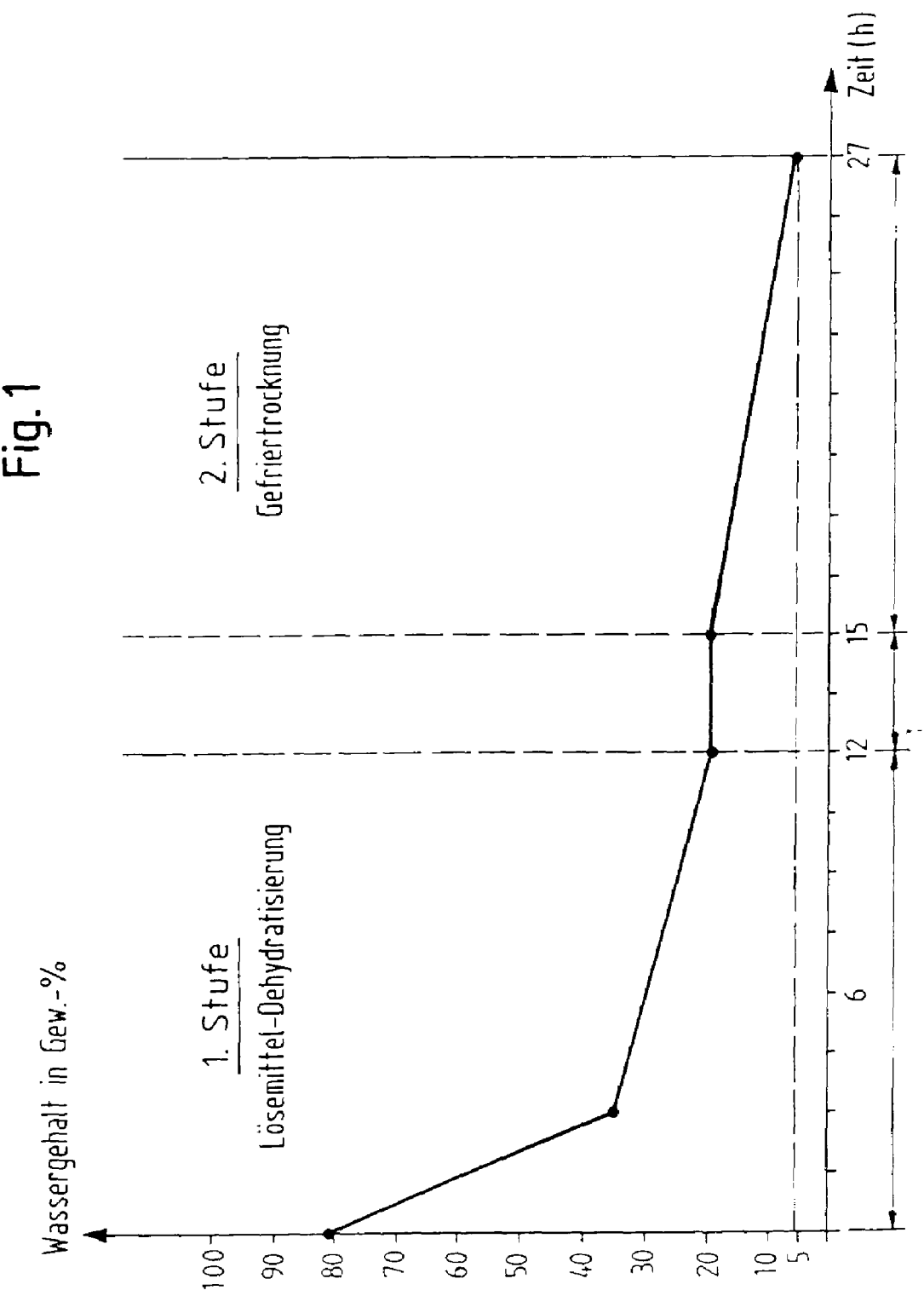

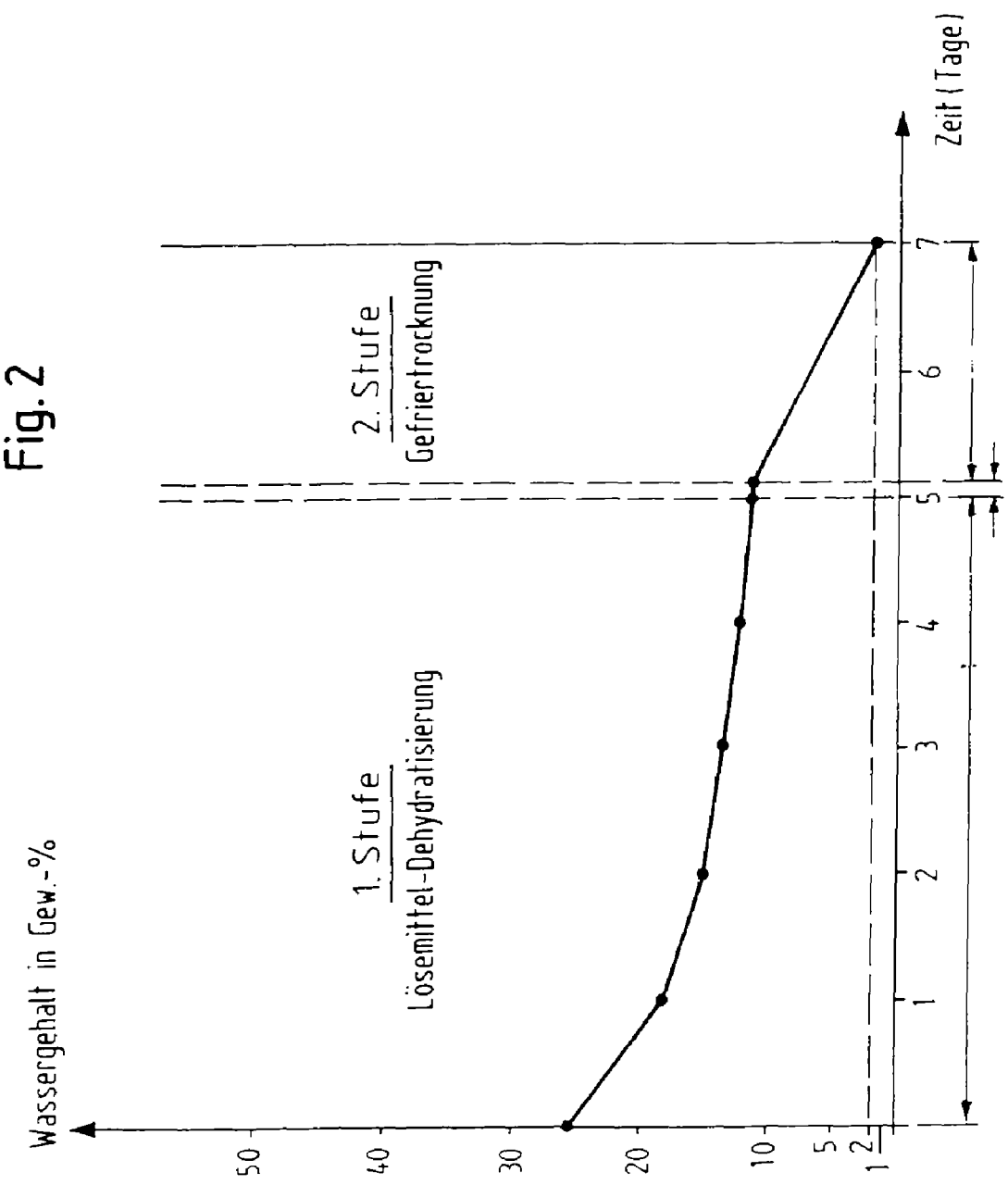

METHOD FOR DEHYDRATING BIOLOGICAL TISSUE FOR PRODUCING PRESERVED TRANSPLANTS

CROSS-REFERENCE TO RELATED APPLICATIONS

This application is the U.S. National Phase of PCT/EP00/07078 filed Jul. 24, 2000, which in turn claims priority of German Patent Application DE 199 40 426.7 filed Aug. 26, 1999, the contents of which are incorporated herein by reference.

FIELD OF THE INVENTION

The present invention relates to a method for dehydrating biological tissue for producing preserved transplants.

BACKGROUND OF THE INVENTION

Methods for the dehydration of biological tissue for producing preserved transplants deliver autografts, allografts or xenografts which are available to the surgeon at any time as required.

Transplants should have a morphological structure very similar to the native tissue, for example skin, tendons, bones and their properties should largely correspond to those of the native tissue. The required properties include internal surface, handling capability and elasticity. Furthermore, still further criteria must also be observed in the producing of preserved transplants. The transplant must be able to be stored in a sterile condition for practically any length of time while maintaining its properties. It must furthermore have a certain resistance to degradation by the receiving organism so that it can function as a guide rail for tissue sprouting in.

A known method for dehydrating biological tissue for producing preserved transplants makes use of freeze drying. The aqueous tissue is frozen at approximately −25° C. to −40° C. and the ice which arises is removed by sublimation in a vacuum. The resulting tissue has a low water content. It can be stored in a sterile condition for a long period while maintaining its properties and is available, when required, as a ready-to-use preserved transplant.

This method is, however, connected to disadvantages. With areal collagenic tissue, for example with dura mater, relatively thick spongiform materials are created which makes their handling more difficult. The collagenic starting tissue is a swollen fibrous network in the moist state and this state is fixed during deep freezing. The ice crystals which form between the fibers and the fibrils during freezing loosen the fiber structure. During the subsequent sublimation, cavities arise in the tissue which degrade its properties in comparison with the native tissue. In particular the elasticity is substantially degraded. Furthermore, as a result of partial bonding of the fibrils, the inner surface is dramatically degraded. The resulting product thereby only has a greatly reduced guide rail effect for inwardly sprouting connective tissue when used as a transplant.

Due to these disadvantages of freeze drying, a method is described in DE 29 06 650 C2 in which the collagenic tissue is dehydrated with an organic solvent which can be mixed with water. In this method, a gradual de-swelling of the biological tissue takes place during the successive extraction of the water so that the native fibrillary structure is maintained and no bonding of the fibrils occurs. Consequently, the inner surface of the tissue dehydrated in this way corresponds to that which the native tissue has. The elasticity is likewise substantially maintained. In this method, however, a number of extraction steps are required for the far-reaching dehydration in which the solvent has to be replaced over and over again. With spongiosa bones up to 20 extraction steps are required. This represents a time-consuming process. The frequent solvent changes are also labor and cost intensive. Furthermore, an environmentally friendly recycling method is required for the solvent.

A method is described in DE 38 35 237 C1 in which bovine pericard tissue is dehydrated with acetone, dried in air, rehydrated with water and then freeze dried. First, this method is relatively complex and, second, the same disadvantages occur as were described above with the method of freeze drying, since the rehydrated tissue is freeze dried.

SUMMARY OF THE INVENTION

The object of the present invention is the providing of a method for dehydrating biological tissue for producing preserved transplants in which the native structure of the collagenic tissue is largely maintained, on the one hand, and which is less time-consuming and less labor and cost intensive, on the other hand.

To satisfy this object, a method is provided for dehydrating biological tissue for producing preserved transplants in which, in a first step, the tissue is partly dehydrated with an organic solvent which can be mixed with water and, in a second step, the tissue is further dehydrated by freeze drying.

It is possible with this two-step method to achieve a faster dehydration, which is also more favorable under labor and cost aspects, while simultaneously maintaining the native structure, in particular the inner surface, and the elasticity of the collagenic material. The number of extraction steps with the organic solvent can be considerably lowered in comparison with a preservation method in which dehydration takes place only with organic solvents. The preservation process is thereby considerably shortened, solvent is saved and, consequently, less solvent is led to recycling and also frequent, labor-intensive changing of the solvent with added water for fresh solvent is saved. The freeze drying step additionally provides the advantage of simple handling due to the drying with fully automated apparatuses. The initially named disadvantages of freeze drying surprisingly do not occur with the method in accordance with the invention.

DETAILED DESCRIPTION OF THE INVENTION

Human or animal tissue can be used as the biological tissue in the method of the invention, for example skin, dura mater, fascia lata, tendons, vessels, cartilage, pericard, bones and plates made of bone, nails, pins, screws. This tissue consists of collagen or of collagen and mineral components. The transplants produced in accordance with the method of the invention are available to the surgeon at any time.

The tissue is preferably dehydrated in the first step with the organic solvent which can be mixed with water to a water content in the range from 10 weight percent to 25 weight percent. With soft tissue such as skin, dura mater, fascia lata, dehydration is preferably carried out to a water content in the range from 17 weight percent to 20 weight percent. With hard tissue such as bone, in particular spongiosa bone, dehydration is preferably carried out to a water content in the range from 10 weight percent to 15 weight percent, with, as is to be expected, the structure of the native tissue being maintained. However, it is surprising that the subsequent freeze drying in the second step for the further dehydration up to the desired water content of less than 8 weight percent, which is as low as possible, does not have a negative effect on the tissue structure.

Methanol, ethanol, propanol, isopropanol, acetone, methyl ethyl ketone or their mixtures can be used, for example, as solvents in a manner known per se. Preferably, acetone is used as an organic solvent which can be mixed with water. The solvent used should have a water content which is as low as possible, it should preferably be free of water. The dehydration with the solvent is carried out at temperatures in the range from 0° C. to 70° C. depending on the solvent used. The dehydration of the first step preferably takes place at room temperature.

The tissue is preferably exposed to a vacuum after the dehydration of the first step before it is deep frozen to temperatures from approximately −25° C. to −40° C. The organic solvent is thereby largely removed from the tissue.

In the dehydration in particular of spongiosa bone, it can be advantageous to simultaneously carry out a treatment with ultrasound, vibrators or rockers in the first step during the dehydration with the organic solvent. This promotes a better penetration of the solvent into the fine passages of the spongiosa bone and thereby the degreasing and the dehydration. For the same purpose, an overpressure, alternating pressure or underpressure can also be applied. It can furthermore be advantageous to carry out a vacuum treatment before the first extraction step and after every extraction step before dehydration is carried out with fresh solvent in the next step. This also promotes degreasing and a better exchange of the aqueous organic solvent in the passages with fresh organic solvent. All these measures can also be carried out with soft tissues.

The freeze drying in the second step takes place in a conventional freeze drying unit. The partly dehydrated tissue is therein gradually brought to temperatures from, for example, −25° C. to −40° C. and the ice produced in the tissue is removed by sublimation by applying a vacuum. As already stated further above, a vacuum is preferably applied before the freeze drying, that is before the cooling of the tissue to low temperatures. In this way, the solvent is removed from the tissue in part. The freeze drying follows on from this.

The invention will be explained in more detail with reference to the following examples and to FIGS. 1 and 2. FIGS. 1 and 2 are diagrams in which the time curve of the dehydration of the tissue in the examples is shown. The time in hours or days is entered on the abscissa and the water content in weight percent relative to the total weight of the material to be dehydrated on the ordinate.

EXAMPLE 1

Dura mater is removed from the human body and liberated in a manner known to one skilled in the art from antigenic substances and enzymes. For preservation, the tissue parts cleaned in this manner are treated twice for six hours at a time by being placed into anhydrous acetone at room temperature. The solvent quantity amounts in each case to 500% of the wet weight of the tissue, with a de-swelling of the tissue taking place from 0.65 mm to 0.57 mm. The water content at the completion of this first dehydration step amounts to 20 weight percent.

In the second step, the tissue is cooled for three hours to −40° C. in a freeze drying unit. Then, a vacuum of 1.2 mbar is applied for removing the ice formed in the tissue by sublimation. The shelf temperature amounts to 35° C. The water content after the second step, which takes a total of 15 hours, amounts to 6 weight percent. The thickness of the tissue amounts to 0.54 mm and the inner surface is 20 m2/g. The course of dehydration is shown in FIG. 1.

After packing in moisture-tight pouches and after sterilizing with gamma rays with a minimum dosage of 15 Kgry, the preserved dura mater can practically be stored without limitation and is ready for use for transplants.

If, instead, the dehydration of the dura mater is carried out only with acetone to the same water content of 6 weight percent, three extraction steps of 12 hours each must be conducted.

EXAMPLE 2

A spongiosa bone is prepared in a suitable manner known to one skilled in the art. For preservation, the prepared bone is treated five times for 24 hours each time with anhydrous acetone at room temperature. The solvent quantity amounts to 500% of the wet weight of the bone in each case. After this treatment, the water content amounts to 12 weight percent. The bone is subsequently cooled for 3 hours to −40° C. in the second step and then a vacuum of 1.2 mbar applied for removing the ice formed in the bone by sublimation. The shelf temperature amounts to 35° C. The water content after the second step, which takes a total of 48 hours, amounts to 2 weight percent. The dehydration course is shown in FIG. 2.

If, instead, the dehydration of the spongiosa bone is carried out only with acetone, then up to 20 extraction steps of 24 hours each are required, with approximately 60 ltrs. of acetone being required per 1 kg of bone.

What is claimed is:

1. A method for dehydrating a biological tissue for producing preserved transplants, comprising the steps of:
   (a) dehydrating the tissue to a water content in a range of 10 weight percent to 25 weight percent by subjecting the tissue to an extraction with an organic solvent which can be mixed with water; and
   (b) dehydrating the tissue further by freeze drying.

2. A method in accordance with claim 1, wherein, said organic solvent is selected from the group consisting of: methanol, ethanol, propanol, isopropanol, acetone, methyl ethyl ketone and mixtures thereof.

3. A method in accordance with claim 1, wherein the tissue is dehydrated in step (a) at a temperature from 0° C. to 70° C.

4. A method in accordance with claim 1, further comprising the step of subjecting the tissue to a vacuum treatment before step (b).

5. A method in accordance with claim 1, further comprising the step of subjecting the tissue to a vacuum treatment before step (a) and after step (a).

6. A method in accordance with claim 1, wherein the tissue is subjected to a treatment with ultrasound, with a vibrator or with a shaker during the extraction with the organic solvent in step (a).

7. A method in accordance with claim 1, wherein an overpressure, an alternating pressure or an underpressure is applied during the extraction with the organic solvent in step (a).

* * * * *